United States Patent [19]

Flood

[11] Patent Number: 5,019,130
[45] Date of Patent: May 28, 1991

[54] SUBSTITUTED N-ARYL PYRROLES IN OXIDATIVE HAIR DYE COMPOSITIONS

[75] Inventor: Lawrence A. Flood, Norwalk, Conn.

[73] Assignee: Clairol Incorporated, New York City, N.Y.

[21] Appl. No.: 431,962

[22] Filed: Nov. 3, 1989

[51] Int. Cl.$^5$ ...................... A61K 7/13; C07D 209/04
[52] U.S. Cl. ............................. 8/423; 8/649; 548/416; 548/452; 548/469
[58] Field of Search ............................................. 8/423

[56] References Cited

U.S. PATENT DOCUMENTS

| | | | |
|---|---|---|---|
| 2,725,378 | 11/1955 | Reed | 542/451 |
| 4,560,769 | 12/1985 | Menig et al. | 548/560 |
| 4,808,190 | 2/1989 | Grollier et al. | 8/423 |

OTHER PUBLICATIONS

J. S. Keily and S. Huang, "The Synthesis of Methyl 1-Aryl-2-Pyrrolecarboxylates", *J. Heterocyclic Chem.*, 24 (1987) pp. 1137–1139.

A. R. Katritzky, *Handbook of Heterocyclic Chemistry*, Chap. 3.3, Pergamon Press, New York (1985), pp. 243–291.

N. Clauson-Kaas and Limborg, "The Alkoxylation of Furans with a Negative Substituent . . . ", *Acta Chem. Scandinavica*, 6 (1952), pp. 551–555.

S. Ram et al., "A General Procedure for Mild and Rapid Reduction of Aliphatic and Aromatic . . . ", *Tetrahedron Letters*, 25, No. 32 (1984) pp. 3415–3418.

Elderfield, et al., "The Chemistry of Pyrrole and Its Derivatives", *Heterocyclic Compounds*, vol. 1, Chapter 6 (1967), pp. 277–342.

*Chemical Abstracts*, 47: 7482f.

*Primary Examiner*—A. Lionel Clingman
*Attorney, Agent, or Firm*—S. Nolan; C. J. Zeller

[57] ABSTRACT

The coloring of human hair and other keratinaceous substrates can be carried out efficiently using compositions containing certain N-aryl pyrroles as dye couplers or developers.

17 Claims, No Drawings

SUBSTITUTED N-ARYL PYRROLES IN OXIDATIVE HAIR DYE COMPOSITIONS

BACKGROUND

The coloring of keratinaceous fibers with oxidative dyes is usually carried out by the use of mixtures of couplers and primary intermediates (developers). These are chemical species which react with each other or with other chemical species to produce highly colored molecules of larger size. The efficiency of coloring by the couplers and developers is directly related to their functionality, i.e., the probability of interaction, and this is enhanced by the presence of multiple sites for coupling and/or other dye-forming reactions.

Several references deal with the production or use of pyrroles and N-aryl pyrroles.

J. S. Kiely and S. Huang in "The Synthesis of Methyl-1-Aryl-2-pyrrolecarboxylates", *J. Hetrocyclic Chem.*, 24 (1987), pp. 1137-9 disclose the production of chemical intermediates whose structures generally resemble

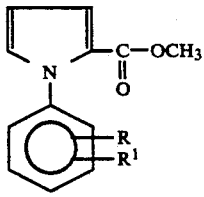

wherein R and $R^1$ may be hydrogen, alkyl, phenyl, acetoxyphenyl, methoxy, or nitro moieties. These compounds are not discussed by the authors as useful in hair coloring.

The general chemistry of substituted pyrroles is described in R. C. Elderfield, ed., "Heterocyclic Compounds, Vol. 1", Chapter 6, John Wiley & Sons, Inc., New York, 1967 and in A. R. Katritzky, "Handbook of Heterocyclic Chemistry", Chapter 3.3, Pergamon Press, New York, 1985. Syntheses of N-aryl Pyrroles are detailed by N. Clauson-Kaas and F. Limborg, *Acta Chem. Scand.*, 1952, 6, 551; and by S. Ram and R. E. Ehrenkaufer, *Tet. Lett.*, 1984, 25, 3415. In *Chemical Abstracts* 47: 7482f, N. Elming and N. Clauson-Kaas disclose methods of making pyrroles from furans. Hair coloring is not mentioned.

Italian Patent No. 428,856 deals with the use of certain pyrroles in processes for coloring hair, where melanin-like materials are produced by the action of strong oxidants on the pyrroles.

U.S. Pat. No. 2,725,378 discloses pyrrole dyes having methine linkages. The dyes are made by condensing dimethylpyrroles with pyrrolealdehydes. The dyes are useful in photographic processing.

U.S. Pat. No. 4,560,769 refers to pyrroles of the formula:

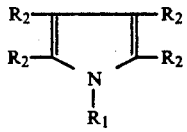

in which $R_1$ and $R_2$ may be H, $C_{1-8}$ alkyl, $C_{7-12}$ alkylaryl, $C_{7-12}$ aralkyl or phenyl groups. The pyrroles are produced by reacting ammonia or $R^1$-$NH_2$ with an $R_2$-substituted 1,4-dihydroxy-2-butene.

U.S. Pat. No. 4,567,272 teaches couplers for human hair dyeing among which are dyes of the formula:

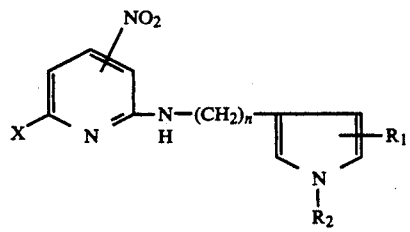

wherein X is H, $C_{1-3}$ alkoxy or $N(R^1)_2$. $R_1$ and $R_2$ are H or $CH_3$ and $n=0-3$.

The disclosures of the publications discussed herein are hereby incorporated by reference, unless otherwise indicated.

THE INVENTION

It has been discovered that the efficiency of certain dyeing systems can be improved via the incorporation therein of compounds of formula I, as set out below, as well as salts and other useful derivatives thereof.

Thus, the invention concerns compositions and methods which employ the subject compounds and their analogs.

In preferred embodiments, specific pyrroles, such as the developer 1-(2-hydroxyethyl amino,5-aminophenyl)pyrrole, and the coupler 1-(2-hydroxy-4-aminophenyl)pyrrole are used with appropriate auxiliary reactants to produce respectively, magenta and blue-violet colors on hair.

ADVANTAGES

Use of the compounds of the invention produces dye formulations and methods which yield dyeouts which are permanent under oxidative conditions.

Surprisingly, the pyrrole substituent in the compounds of the invention contributes to increased stability against air oxidation in systems in which the phenyl group bears at least two OR or $N(R)_2$ type groups. As examples, systems containing meta-aminophenol, meta-diamine, para-aminophenol, or para diamine substituents or other similar species show enhanced storage stability in comparison with non-pyrrole containing analogs.

In addition, pyrrole-containing compounds of the invention also yield more intense (i.e., more deeply colored) dyeouts than corresponding non-pyrrole containing analogs. This is especially surprising in view of the lower molar concentrations of the dyes that were used (due to their higher molecular weight) versus the standards.

The more stringent conditions generally associated with some oxidative dyeing systems—e.g., pH of greater than 9.0 using hydrogen peroxide—can be avoided using the invention. pH's of about 4.0 to about 7.0 are operable, particularly in the presence of certain peroxide-free oxidants, without loss of intensity.

Since the pyrrole substituent provides additional aromatic sites for electrophilic coupling, the compounds of the invention act as, at least, binuclear electrophilic systems. Most standard benzenic couplers are only mononuclear electrophilic systems, with only single sites available for electrophilic coupling.

These and other advantages and aspects of the invention will become more apparent after consideration of the following description and claims.

DESCRIPTION OF THE INVENTION

The invention deals with compositions and methods for coloring keratinaceous substrates, preferably human hair. This description will deal principally with the useful compounds, compositions containing them and conditions and processes involving their use and the types of substrates to be treated.

Unless stated otherwise, all percentages stated herein are weight percentages, based on total composition weight. The higher molecular weights of the pyrrole compounds versus the standards therefore means that much lower molar concentrations of these compounds are being used as compared to the standards.

COMPOUNDS

The compositions and methods of the invention employ at least one compound of formula I:

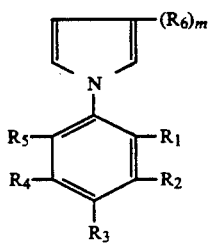

(I)

wherein at least two of $R_1$, $R_2$, $R_3$, $R_4$ and $R_5$ are not hydrogen and wherein they are otherwise independently selected from the group: H, OH, $NH_2$, halogen, $C_{1-4}$ alkyl, $C_{1-4}$ alkoxy, $C_{1-4}$ hydroxyalkyl, $NR_7R_8$, in which $R_7$ is H, $C_{1-4}$ alkyl or $C_{1-4}$ hydroxyalkyl and $R_8$ is $C_{1-4}$ alkyl, $C_{1-4}$ hydroxyalkyl, or $-O(CH_2)_nOR$, in which R is H or $C_{1-4}$ alkyl, and $n=1-3$; $R_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1-6 carbon atoms), $C_{1-6}$ hydroxyalkyl or $C_{1-6}$ alkenyl groups; and $m=1-4$.

By "halogen", applicant means any of the Periodic group termed halogen i.e., Cl, Br, I, and F—with Cl and Br preferred.

One preferred group of compounds are those conforming to formula I in which at least one of $R_1$, $R_2$, $R_3$, $R_4$, or $R_5$ is an OH, $C_{1-4}$ alkoxy, $-O(CH_2)_n-OR$, or $NR_7R_8$ groups, as defined above for formula I.

The pyrroles of the invention are produced via the Clauson-Kaas process Ref: N. Clauson-Kaas and F. Limborg, *Acta. Chem. Scand.*, 1952, 6, 551. (previously cited). Useful starting materials for their synthesis are the appropriately substituted anilines, for example p-aninoacetanilide and 2,5-dimethoxytetrahydrofuran. Kiely and Huang, cited supra, give a review of the scope of the reaction.

Compounds of formula II are a preferred group. Formula II is:

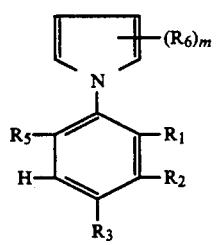

(II)

wherein $R_1$, $R_2$, and $R_3$ are each independently H, OH, $NH_2$, $C_{1-4}$ alkyl, $C_{1-4}$ hydroxyalkyl, or $NR_7R_8$, in which $R_7$ is H, $C_{1-4}$ alkyl or $C_{1-4}$ hydroxyalkyl, and $R_8$ is $C_{1-4}$ alkyl or $C_{1-4}$ hydroxyalkyl, with the proviso that at least two of $R_1$, $R_2$, $R_3$ and $R_5$ not be H;

$R_5$ is H, OH, $OCH_3$, or $NH_2$; and $R_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contains 1-6 carbon atoms), $C_{1-6}$ hydroxy alkyl, or $C_{1-6}$ alkenyl; and $m=1-4$.

Depending on the particular substitution pattern, these compounds may either be couplers or developers in the dyeing compositions of the invention.

Another preferred group of compounds conforms to Formula III:

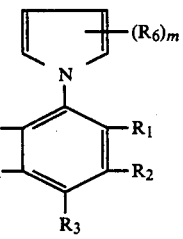

(III)

wherein at least one pairing of $R_1$ and $R_2$, $R_2$ and $R_3$, $R_3$ and $R_4$ and $R_4$ and $R_5$ is joined to form a group of the formula $-O-(CH_2)_n-O-$, in which $n=1-3$; and $R_6$ and all non-paired groups on the benzene ring are independently H, $C_{1-4}$ alkyl groups $NH_2$, OH, or $NR_7R_8$ and $m=1-4$.

It is contemplated that paired R groups may be linked, so that, taken together, they form, e.g., a $-O-CH_2-O-$ bridge—i.e. a heterocyclic fused ring.

These compounds will act as couplers in a dyeing compositions.

Yet another preferred group of compounds has formula IV:

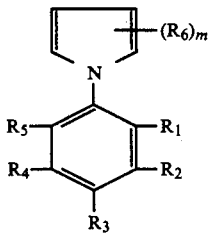

(IV)

wherein $R_2$ and $R_4$ are both OH, $NH_2$ or $NR_7R_8$ in which $R_7$ is H, $C_{1-4}$ alkyl, $C_{1-4}$ alkoxy, $C_{1-4}$ hydroxyalkyl, and $R_8$ is $C_{1-4}$ alkyl or $C_{1-4}$ hydroxyalkyl;

$R_1$, $R_3$, and $R_5$ are each independently H, halogen, or alkyl;

$R_6$ may be H, OH, $C_{1-6}$ alkyl, phenyl, halogen, carboxy, carboxyaldehyde, nitro, amino, $C_{1-6}$ alkoxy, dialkylaminoalkyl (in which the alkyl groups contain 1-6 carbon atoms), $C_{1-6}$ hydroxyalkyl, or $C_{1-6}$ alkenyl, and m=1-4.

These compounds will act as couplers in dyeing compositions.

Lastly, a group of compounds represented by formula V may be used. Formula V is:

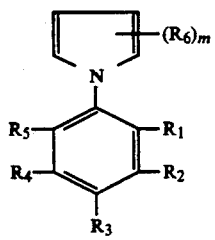

(V)

wherein $R_1$ and $R_4$ are both $NH_2$, OH, or $NR_7R_8$ in which $R_7$ is H, $C_{1-4}$ alkyl, $C_{1-4}$ alkoxy, or $C_{1-4}$ hydroxyalkyl and $R_8$ is and $C_{1-4}$ alkyl, or $C_{1-4}$ hydroxyalkyl;

$R_2$, $R_3$, and $R_5$ are each independently H, halogen, $C_{1-4}$ alkyl, or $C_{6-24}$ aryl;

$R_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1-6 carbon atoms), $C_{1-6}$ hydroxyalkyl, or $C_{1-6}$ alkenyl and m=1-4.

By "aryl," applicant means aronatic moeities containing single benzene rings as well as fused, bridged and C—C linked systems. These systems may be substituted or substituted with halogen, $C_{1-14}$ alkyl, amine and other groups.

These compounds act as developers in oxidative dye formulations.

Compounds of formula II and V are highly preferred. Compounds of formula II are most preferred.

It should be noted that, while applicant refers to compounds having the formulas indicated above, he also contemplates the use of salts, e.g., the hydrocloride salts and other derivatives, of the compounds discussed. Mixtures are operable.

Table I sets forth substituent groups in a series of pyrroles which were evaluated as hair dye components in accordance with the invention. These compounds conform to formula VI:

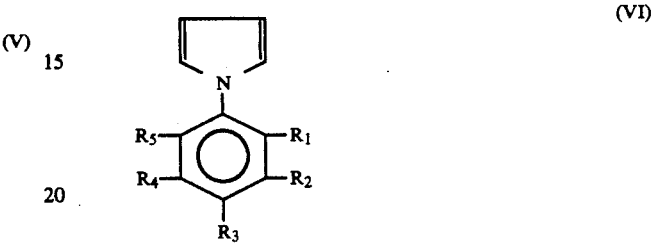

(VI)

In the hair dyeing evaluation 0.1% of the test compound and an equimolar concentration of the co-reactant either p-phenylenediamine (PPD) when the test compound was a coupler or 5-amino-o-cresol (AOC) when the test compound was a developer) were dissolved in 30% aqueous etharol. At the time of dyeing an equal volume of 6% hydrogen peroxide was added and the mixture adjusted to pH 9.5 with monoethanolamine.

A 2 g tress of gray hair was then dyed with 5 g of this solution for 25 minutes. After this time, the tress was removed, rinsed with water and air dried. The color of these tresses with the various test compositions are recorded in Table I.

TABLE I

Substutients for Compounds Evaluated As Hair Dye Couplers or Developers

| | | Substituents in Formula VI | | | | |
|---|---|---|---|---|---|---|
| $R_1$ | $R_2$ | $R_3$ | $R_4$ | $R_5$ | Co-reactant | Color |
| $NH_2$ | H | $NH_2$ | H | H | PPD | Dark Blue |
| $NH_2$ | H | H | H | $NH_2$ | PPD | Dark Blue |
| H | $NH_2$ | H | $NH_2$ | H | PPD | Red-Brown |
| $NH_2$ | H | H | $NH_2$ | H | AOC | Red-Violet |
| $NH(CH_2CH_2OH)$ | H | H | $NH_2$ | H | PPD | Violet-Brown |
| $NH_2$ | H | H | H | OH | PPD | Violet |
| OH | H | $NH_2$ | H | H | PPD | Deep Violet |
| H | $NH_2$ | OH | H | H | PPD | Olive Green |
| OH | H | H | $NH_2$ | H | AOC | Red-Orange |
| $OCH_3$ | H | $NH_2$ | H | H | PPD | Silver-Gray |
| $OCH_3$ | H | H | $NH_2$ | H | PPD | Gray-Brown |
| $CH_3$ | OH | H | H | H | PPD | Blue-Gray |
| OH | H | $CH_3$ | H | H | PPD | Dark Blue |
| OH | H | H | $CH_3$ | H | PPD | Violet-Brown |
| H | OH | $CH_3$ | H | H | PPD | Dark Blue |
| $CH_3$ | H | OH | H | H | PPD | Gray Violet |
| $NH_2$ | H | $CH_3$ | H | H | PPD | Gray-Brown |
| $CH_3$ | $NH_2$ | H | H | H | PPD | Violet-Brown |
| $CH_3$ | H | $NH_2$ | H | H | PPD | Violet-Brown |
| $CH_3$ | H | H | $NH_2$ | H | PPD | Violet-Brown |
| H | $NH_2$ | $CH_3$ | H | H | PPD | Gray-Brown |
| $CH_3$ | H | H | H | $CH_3$ | PPD | Violet-Gray |
| H | OH | H | H | H | PPD | Blue-Gray |
| $NH_2$ | H | H | H | H | PPD | Gray-Violet |

The compounds of the invention will generally be used in dyeing or other coloring systems in quantities ranging from about 0.01 to about 10 wt. % and preferably from about 0.1 to about 3 wt. %.

The compounds of the invention are referred to as "couplers" or "developers" depending on the configuration of substituent groups. Developers have the oxidizable substituents, e.g., OH NH$_2$ etc., oriented ortho or para to each other, where they can readily interact upon oxidation and produce color.

Couplers have single substituents or substituents oriented meta to each other, where little interaction is possible. Couplers therefore do not easily oxidize and do not produce color in oxidation. Instead they are used to modify the colors produced by developers by reacting directly with the oxidized intermediates.

Their binuclear character makes the compounds of the invention particularly effective, by adding additional reaction sites.

The terms "oxidative coloring", "oxidation dyes", and the like are employed to refer to coloring systems in which color is developed following an oxidative process. Prior to this process, the system has no color. Generally, the dye intermediates are mixed with the oxidant immediately prior to use and the mixture then applied to the hair. Color develops over 20 to 30 minutes. The hair is dyed permanently by this process (i.e., the color cannot be shampooed out.)

OTHER COUPLERS/INTERMEDIATES

The substituted N-arylpyrroles of the invention are useful as such, i.e., with a suitable oxidant, they can function alone to color hair or other substrates.

However, the subject pyrroles can also be used in combination with one or more additional couplers, developers or other species to produce colorant molecules of significantly greater color variation.

Useful compounds to be employed along with the pyrroles of the invention are aromatic compounds containing from 6 to 24 carbon atoms in the ring(s) and up to 30 carbon atoms in substituent groups. Preferred compounds contain benzene, naphthalene, and/or anthracene nuclei bearing from 2 to 20 substituents.

One particularly useful group of compounds is di-substituted benzenes, such as paraphenylene diamine (PPD), para-aminophenol (PAP), meta-aminophenol, paraamino-ortho-cresol, resorcinol, m-phenylenediamine and the like.

Another useful group is naphthols and pyridines. The compounds alpha-naphthol, 2,6-dihydroxypyridine, and 2,5-diaminopyridine are illustrative of this group.

Mixtures of two or more of the compounds discussed above can be employed with one or more of the pyrrole species of the invention.

When present, these auxiliary agents, e.g., p-phenylenediamine, resorcinol, and alpha-naphthol are present in amounts ranging from about 0.001 to about 10 wt. %, preferably from about 0.1 to about 3 wt. %.

OXIDANTS

The oxidizers used in the invention serve to generate color from the intermediates and couplers. Useful agents of this type are peroxides, metal salts, per salts and the like having the requisite activity.

Conventional peroxide oxidants can be used herein, and it is preferred that hydrogen peroxide, urea peroxide and the like be used. Solid adducts of peroxide are useful when a powdered oxidant is preferred.

Among other useful oxidants are alkali metal periodates and iodates e.g., NaIO$_4$ and KIO$_3$. Sulfur-containing anions, such as persulfates and the like are, useful. NH$_4$S$_2$O$_8$ is a preferred compound among this group.

Mixtures are operable.

The oxidant component of the composition will generally be present in an amount ranging from about 0.01 to about 10 wt. %, preferably from about 0.1 to about 6 wt. %.

While this system operates very effectively in the generally accepted dyeing range of pH 9 to pH 10, the pH of the inventive system may, if desired, be reduced to a value lower than that employed when other oxidative coloring systems are employed.

The nature of the oxidant employed will be a consideration in the selection of suitable pH's for operation.

Accordingly, the need for large amounts of harsh alkalizing agents, such as concentrated ammonia, may be eliminated, if desired.

The pH of the subject compositions is adjusted to useful values using one or more of such agents as monoethanolamine, citric acid, ammonia and phosphoric acid. Monoethanolamine and phosphoric acid are preferred.

Buffers, e.g., phosphate and citrate and the like, and other pH stabilizers may be employed in the compositions and methods of the invention.

Mixtures are contemplated.

DYEING ASSISTANTS

By "dyeing assistants", applicant means additional developer and other agents which facilitate the formulation or modification of color in or on the substrate.

SOLVENTS

While water is a principal diluent, the compositions and methods of the invention generally employee one or more solvents. These solvents solubilize one or more ingredients so that a reaction may occur more readily and so that the composition can penetrate the hair or other substrate more readily.

Useful solvents include C$_{1-20}$ mono- or polyhydric alcohols and their ethers, with monohydric and dihydric alcohols and their ethers preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and the like. Mixtures may be used.

The amount of solvent component will generally be from about 1 to about 50 wt. %.

The compositions of the invention may be stored and handled as concentrates with dilution or suspension in suitable media being carried out just prior to application. Application via spraying, dipping, brushing, swabbing, combing, pouring, or combinations of these, is contemplated.

OTHER EXCIPIENTS

In addition to the solvent(s) used, the invention may also involve the use of additional agents which do not adversely affect the functions of the ingredients discussed above and are usually added to compositions for dyeing keratinous fibers. Among these are surfactants, perfumes, flow control agents, stabilizers and other properties-enhancing agents.

Additional colorants, while not preferred, may be added so long as they do not interfere with the performance of the pyrroles or any other auxiliary couplers/intermediates in the system. When used, the excipients discussed here will be present in amounts ranging from about 1 to about 50 wt. %, with about 1 to about 20% being optimal.

SUBSTRATES

The substrates to be color treated via contacting with the dyeing systems of the invention are generally keratinaceous in character. Mammalian, preferably human, hair is a preferred substrate. However, fur, wool and other fibrous materials of animal origin are contemplated.

The hair to be treated may be "living", i.e., on a living body, or may be "dead", i.e., in a wig, hair piece or other aggregation of non-living hair fibers.

While treatment of the hair in it's natural state is envisioned, the hair may be pretreated. Thus, hair which has been bleached, previously colored, relaxed, permed or otherwise chemically modified may be colored in accordance with the invention.

COLORING CONDITIONS

The conditions under which the subject oxidative coloring systems are used may vary widely in accordance with the preference of the hair colorist. In general, solutions or dispersions of the color-forming ingredient(s) and oxidant(s) are mixed immediately prior to use and will be contacted with the hair or other substrate for a period of about 5 to about 60 minutes, with about 20 to about 40 minutes preferred. Subsequent treatments may be used to enhance color intensity.

Contacting of the hair with the coloring component(s) and oxidant(s) is usually carried out simultaneously. However, the process can be done in two steps where the coloring components are preceded or followed by contacting with one or more oxidants, such as those discussed above. In such cases, it is preferred that the oxidant be used following contact. The oxidant or other dye assistant is usually used for about 5 to about 40 minutes.

Afterward, one or more rinses can be used to stop the reaction and facilitate removal of the reagents.

Further coloring may be carried out after the rinsing operation(s) but is generally not necessary.

Following the coloring and rinsing steps, the hair may be conditioned and/or treated with setting or other formulations. Mechanical treatments such as drying, rolling, combing, and the like may be carried out. Chemical treatment(s) may also be carried out.

EXAMPLES

The following examples illustrate the invention.

Example 1

A solution composed of 20 mg of 1-(2-hydroxy-4-aminophenyl)-pyrrole and 10 mg of p-phenylenediamine in 10 mL of 30% aqueous ethanol was mixed with an equal volume of 6% $H_2O_2$ (adjusted with to pH 9.5 with monoethanolamine (MEA)*. Tresses of bleached and blended gray hair were soaked in the mixture for 25–30 minutes, then rinsed with water and air dried to afford, respectively, a deep blue-violet or deep violet color.

Example 2

A solution composed of 24 mg of 1-(2-hydroxyethyl amino-5-aminophenyl) pyrrole and 15 mg of 5-amino-o-cresol in 10 mL of 30% aqueous ethanol was mixed with an equal volume of 6% $H_2O_2$ adjusted to pH 9.5 with monoethanolamine*. Blended gray hair was soaked for a period of about 25–30 minutes, then water rinsed and air dried to afford a magenta dyeout.

Example 3

Solutions composed of 20 mg of 1-(2-hydroxy-4-aminophenyl) pyrrole and 10 mg of p-phenylenediamine in 10 mL of 30% aqueous ethanol and 25 mL of a 5% aqueous sodium periodate solution were prepared. Both the pyrrole and PPD/Cresol were in solution w/30% aqueous ethanol. Blended grey and bleached hair tresses were then soaked in 3 mL of each of the dye solutions for 10 minutes, followed by soaking for 10 minutes in 3 mL of the periodate solution. The hair was then water rinsed and air dried to afford a dark brown-violet dyeout on both tresses.

Example 4

This example illustrates some of the dyeing and lightfastness properties attained using the pyrrolic couplers of the invention with paraphenylenediamine as developers. The procedure used in conducting these tests was to dissolve 0.1% of the test coupler with an equimolar amount of p-phenylenediamine in 30% aqueous ethanol. At the time of dyeing, an equal volume of 6% $H_2O_2$ solution was added, and the mixture adjusted to pH 9.5 by adding monoethanolamine. The appropriate hair tress (about 2 g) was then immersed in 5 g of the dyeing solution for 30 minutes. After removal from the dye bath, the tress was water rinsed and air dried.

Hunter Tristimulus values were then determined using the Hunter Labscan instrument which records the color of the tress in terms of 'L', 'a' and 'b' values. L measures the intensity of color (white=100, black=0) and 'a' and 'b' the shade or hue (+a=red, −a=green; +b=yellow, −b=blue).

The tresses were then exposed to simulated sunlight for 10 hours in an Atlas Fade-o-meter. After exposure, the Hunter Tristimulus values were again measured and the overall change calculated as below:

$$E^* = \frac{\Delta E}{\Delta E_o} \times 100$$

where $$\Delta E = (\Delta L^2 + \Delta a^2 + \Delta b^2)^{\frac{1}{2}}$$

and ΔL, Δa and Δb refer to the change in L, a and b values caused by exposure to light;

and $\Delta E_o$ is calculated as ΔE except that, in this case, the changes refer to the dyeing process.

Table II shows the various pyrroles evaluated based upon the following structural formula:

TABLE II

Dyeings Using Substituted Pyrroles With Paraphenylenediamine

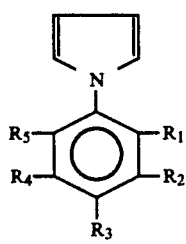

| | Substituents | | | | Hair | | Light-fastness |
|---|---|---|---|---|---|---|---|
| | $R_1$ | $R_2$ | $R_3$ | $R_4$ | $R_5$ | Type | Color | E* |
| A | OH | H | $NH_2$ | H | H | BL | Deep Blue-Violet | −2 |
| | | | | | | BG | Violet | |
| B | $NH_2$ | H | H | H | OH | BL | Violet | −4% |
| | | | | | | BG | Violet | |
| C | H | $NH_2$ | OH | H | H | BG | Yellow-Brown | −16% |
| D | H | OH | H | H | H | BL | Gray-Blue | −17% |
| E | OH | H | $CH_3$ | H | H | BL | Dark Blue | −27% |

BL — Bleached;  BG — Blended Gray Hair

These results show the superior lightfastness of the colors, particularly on gray hair.

Example 5

This examples shows the superior storage stability of solutions containing pyrrole B (Table II). Pyrrole B has the structure:

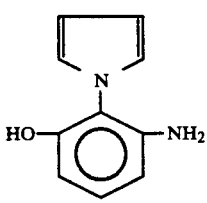

A solution (8.3% w/w) of the pyrrole coupler was prepared in 95% ethanol. This solution was used to prepare a dyeing composition as described in Example 4. The remainder of the solution was stored for 7 weeks at 25°. After this time, a second identical composition was prepared. Both compositions were used to dye hair tresses immediately after their preparation. Results, which are essentially identical, are recorded in Table III.

TABLE III

Stability on Storage in Solution, a Dyeout Comparison

| | | | Tristimulus Values | | |
|---|---|---|---|---|---|
| Conditions[b] | Reactant | Hair Type | L | a | b |
| Initial | PPD | BL | 22.1 | 6.0 | −3.0 |
| After 7 Weeks | PPD | BL | 23.4 | 5.9 | −2.9 |

Under similar storage conditions, solutions containing the conventional couplers m-phenylenediamine or m-amirophenol has precipitated dark colored solids and were unusable for hair dyeing.

Example 6

Table IV sets out the color intensities, as measured by Tristimulus value L, for a series of conventional couplers and intermediates compared to analogous pyrroles.

The dyeings were carried out as described in Example 4, except that with compound V, the P-phenylenediamine (PPD) was omitted and an equimolar concentration of 1-naphthol was used.

TABLE IV

Dyeout Intensity-Relational Comparison

| Compounds | Concn. | Co-Reactant | Tristimulus L Value | L |
|---|---|---|---|---|
| m-aminophenol+ | 0.1% | PPD | 23.2 | +3.6 |
| II, $R_2=R_5=R_6=H$; $R_1=OH, R_3=NH_2$ | 0.1% | PPD | 19.6 | |
| 5-amino-o-cresol+ | 0.1% | PPD | 28.1 | +6.0 |
| IV, $R_1=R_4=R_5=R_6=H$; $R_2=OH, R_3=CH_3$ | 0.1% | PPD | 22.1 | |
| 2-Amino-5-methyl-phenol+ | 0.1% | PPD | 36.8 | +10.6 |
| IV, $R_2=R_4=R_5=R_6=H$ $R_1=OH, R_3=CH_3$ | 0.1% | PPD | 26.2 | |
| p-Aminophenol | 0.1% | 1-naphthol | 44.1 | +4.6 |
| V, $R_2=R_3=R_5=R_6=H$; $R_1=OH; R_4=NH_2$ | 0.1% | 1-naphthol | 39.5 | |

These results show the increase in intensity (decrease in L value) resulting from use of the pyrrolic compounds versus their conventional counterparts.

Example 7

The use of oxidants other than hydrogen peroxide ($H_2O_2$) is illustrated in Table V.

The dyeings were carried out at appropriate pH using PPD and the pyrrole coupler of formula:

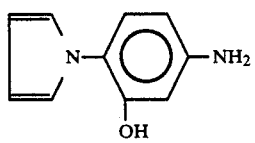

Dyeing solutions were prepared as described in Example 4 except that peroxide was omitted and an aqueous solution of the appropriate oxidants was substituted. pH was adjusted to the values in the Table by either acid or alkali.

2 g tresses were soaked for 10 minutes in 5 g of dye solution and then, without rinsing, 5 g of the oxidant solution was applied for 10 minutes. The tress was rinsed with water and air dried. Tristimulus readings were then taken. The results are recorded in Table V.

These results show that equally effective dyeings are produced at lower pH and with oxidants other than hydrogen peroxide.

TABLE V

Dyeouts with Other Oxidants
(Pyrrole Derivative at 0.2%).

| Oxidant | Hair Type | Color | Tristimulus Values | | |
|---|---|---|---|---|---|
| | | | L | a | b |
| 2.5% KIO$_3$ + 2.5% NH$_4$S$_2$O$_8$ (pH7) | BL | Pinkish Violet | 33.9 | 8.2 | 4.3 |
| | BG | Gray-Violet | 35.0 | 4.2 | 5.1 |
| 5% NaIO$_4$ (pH6) | BL | Dark Brown-Violet | 24.1 | 6.1 | 3.0 |
| | BG | Brown-Violet | 31.0 | 4.4 | 5.2 |

Reasonable variations, such as those which would occur to a skilled artisan, can be made herein without departing from the scope of the invention.

I claim:

1. An oxidative hair dye composition for coloring keratinaceous substrates containing, as a reactive hair dye precusor, at least one compound of formula (I):

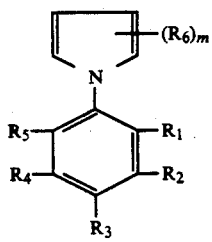

(I)

wherein at least two of $R_1$, $R_2$, $R_3$, $R_4$, and $R_5$ are not hydrogen and wherein they are otherwise independently selected from the group: H, OH, NH$_2$, halogen, $C_{1-4}$ alkyl, $C_{1-4}$ alkoxy, $C_{1-4}$ hydroxyalkyl, NR$_7$R$_8$ (in which R$_7$ is H, $C_{1-4}$ alkyl or $C_{1-4}$ hydroxyalkyl and R$_8$ is $C_{1-4}$ alkyl or $C_{1-4}$ hydroxyalkyl), or —O(CH$_2$)$_n$—OR in which R is H or $C_{1-4}$ alkyl, and n=1–3; R$_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1–6 carbon atoms), $C_{1-6}$ hydroxyalkyl or $C_{1-6}$ alkenyl groups; and m=1–4.

2. The composition of claim 1 wherein at least one of R$_1$ through R$_5$ is an OH, $C_{1-4}$ alkoxy, —O—(CH$_2$)$_n$—OR, or NR$_7$R$_8$ group, as defined in claim 1.

3. The composition of claim 1 wherein the compound conforms to formula (II):

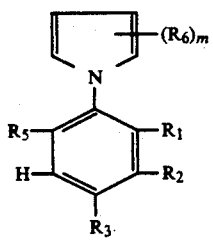

(II)

wherein R$_1$, R$_2$, and R$_3$ are each independently H, OH, NH$_2$, $C_{1-4}$ alkyl, $C_{1-4}$ alkoxy, $C_{1-4}$ hydroxyalkyl or NR$_7$R$_8$ (in which R$_7$ is H, $C_{1-4}$ alkyl, or $C_{1-4}$ hydroxyalkyl and R$_8$ is $C_{1-4}$ alkyl or $C_{1-4}$ hydroxyalkyl alkyl; with the proviso that at least two of R$_1$, R$_2$, R$_3$ and R$_5$ not be H;

R$_5$ is H, OH, OCH$_3$, or NH$_2$;

R$_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1–6 carbon atoms), $C_{1-6}$ hydroxy-alkyl or $C_{1-6}$ alkenyl; and m=1–4.

4. The composition of claim 1 wherein the compound is a coupler of formula III:

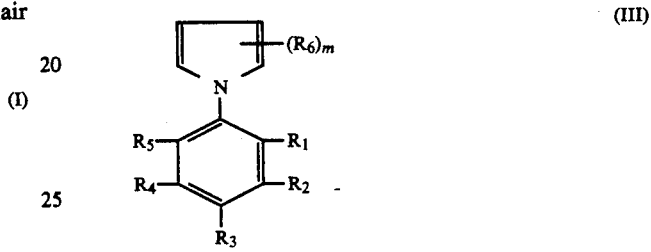

(III)

wherein at least one pairing of R$_1$ and R$_2$, R$_2$ and R$_3$, R$_3$ and R$_4$, and R$_4$ and R$_5$ is joined to form a group of the formula —O—(CH$_2$)$_n$—O—, in which n=1–3;

all non-paired groups on the benezene ring are independently H or $C_{1-4}$ alkyl groups, OH, NH$_2$, or NR$_7$R$_8$ as defined in claim 1; and m=1–4.

5. The composition of claim 1 wherein the compound is a coupler of formula IV:

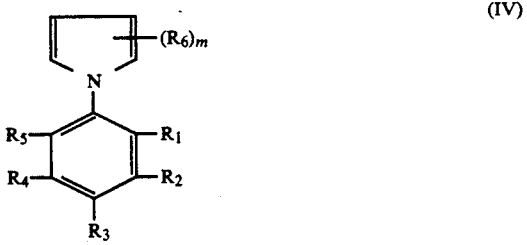

(IV)

wherein R$_2$ and R$_4$ are both OH, NH$_2$, or NR$_7$R$_8$, in which R$_7$ is H, $C_{1-4}$ alkyl, $C_{1-4}$ alkoxy, $C_{1-4}$ hydroxyalkyl, and R$_8$ is $C_{1-4}$ alkyl or $C_{1-4}$ hydroxyalkyl;

R$_1$, R$_3$ and R$_5$ are each independently H, halogen, or alkyl; and R$_6$ may be H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1–6 carbon atoms) $C_{1-6}$ hydroxyalkyl, or $C_{1-6}$ alkenyl, and m=1–4.

6. The composition of claim 1 wherein the compound is a developer of formula V:

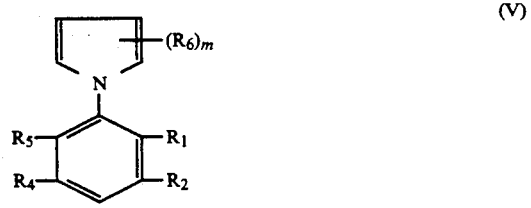

(V)

wherein $R_1$ and $R_4$ are both $NH_2$, OH, or $NR_7R_8$ (in which $R_7$ is H, $C_{1-4}$ alkyl, $C_{1-4}$ alkoxy, or $C_{1-4}$ hydroxyalkyl and $R_8$ is $C_{1-4}$ alkyl, or $C_{1-4}$ hydroxyalkyl);

$R_2$, $R_3$ and $R_5$ are each independently H, halogen, $C_{1-4}$ alkyl, or $C_{6-24}$ aryl;

$R_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1–6 carbon atoms), $C_{1-6}$ hydroxyalkyl, or $C_{1-6}$ alkenyl; and m=1–4.

7. The composition of claim 1 having a pH of about 4.0 to about 10.0.

8. The composition of claim 7 additionally containing at least one developer selected from the group consisting of p-phenylenediamines and p-aminophenols.

9. The composition of claim 1 wherein the compound is a coupler named 1-(2-hydroxy-4-aminophenyl)pyrrole.

10. The composition of claim 9 additionally containing at least one developer selected from the group consisting of p-phenylenediamines and p-aminophenols.

11. The composition of claim 1 wherein the compound is a developer named 1-(2-hydroxyethylamino-5-aminophenyl)pyrrole.

12. The composition of claim 11 additionally containing at least one coupler selected from the group consisting of: 5-amino-o-cresol, 1-naphthol, m-phenylenediamine and resorcinol.

13. A method of oxidatively coloring keratinaceous substrates comprising contacting them with a composition containing at least one compound of formula (I):

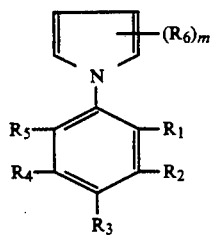

(I)

wherein at least two of $R_1$, $R_2$, $R_3$, $R_4$ and $R_5$ are not hydrogen and wherein they are otherwise independently selected from the group: H, OH, $NH_2$, halogen, $C_{1-4}$ alkyl, $C_{1-4}$ alkoxy, $C_{1-4}$ hydroxyalkyl, $NR_7R_8$ (in which $R_7$ is H, $C_{1-4}$ alkyl or $C_{1-4}$ hydroxyalkyl and $R_8$ is $HC_{1-4}$ alkyl or $C_{1-4}$ hydroxyalkyl), or —O(CH$_2$)$_n$—OR, in which R is H or $C_{1-4}$ alkyl, and is H or 3; $R_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1–6 carbon atoms), $C_{1-6}$ hydroxyalkyl or $C_{1-6}$ alkenyl groups; and m=1–4.

14. The method of claim 13 which employs a compound conforming to any of formulas II-V, as follows:

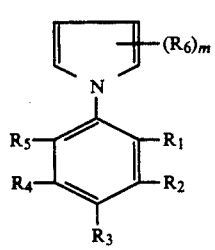

(II)

wherein $R_1$, $R_2$, and $R_3$ are each independently H, OH, $NH_2$, $C_{1-4}$ alkyl, $C_{1-4}$ alkoxy, $C_{1-4}$ hydroxyalkyl or $NR_7R_8$ (in which $R_7$ is H, $C_{1-4}$ alkyl, or $C_{1-4}$ hydroxyalkyl and $R_8$ is $C_{1-4}$ alkyl or $C_{1-4}$ hydroxyalkyl alkyl), with the proviso that at least two of $R_1$, $R_2$, $R_3$ and $R_5$ are not H;

$R_5$ is H, OH, OCH$_3$, or $NH_2$;

$R_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1–6 carbon atoms), $C_{1-6}$ hydroxy alkyl or $C_{1-6}$ alkenyl; and m=1–4; or a coupler of formula:

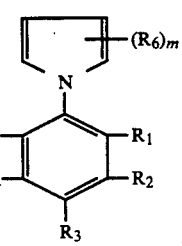

(III)

wherein at least one pairing of $R_1$ and $R_2$, $R_2$ and $R_3$, $R_3$ and $R_4$, and $R_4$ and $R_5$ is joined to form a group of the formula —O—(CH$_2$)$_n$—O—, in which n=1–3;

all non-paired groups on the benzene ring are independently H or $C_{1-4}$ alkyl groups: OH, $NH_2$, or $NR_7R_8$ as defined for formula II and m=1–4; or a coupler of the formula:

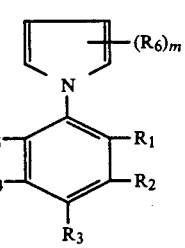

(IV)

wherein $R_2$ and $R_4$ are both OH, $NH_2$, or $NR_7R_8$ (in which $R_7$ is H, $C_{1-4}$ alkyl, $C_{1-4}$ alkoxy, $C_{1-4}$ hydroxyalkyl, and $R_8$ is $C_{1-4}$ alkyl or $C_{1-4}$ hydroxyalkyl);

$R_1$, $R_3$ and $R_5$ are each independently H, halogen, or alkyl; and $R_6$ may be H, OH, $C_{1-6}$ alkyl, phenyl, halogen, carboxy, carboxyaldehyde, nitro, amino, $C_{1-6}$ alkoxy, dialkylaminoalkyl (in which the alkyl groups contain 1–6 carbon atoms), $C_{1-6}$ hydroxyalkyl, or $C_{1-6}$ alkenyl, and m=1–4; or a developer of the formula:

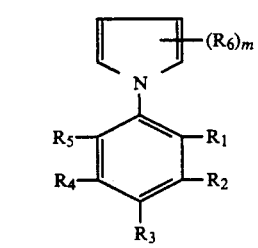

(V)

wherein $R_1$ and $R_4$ are both $NH_2$, OH, or $NR_7R_8$ (in which $R_7$ is H, $C_{1-4}$ alkyl, $C_{1-4}$ alkoxy, or $C_{1-4}$ hydroxyalkyl and $R_8$ is $C_{1-4}$ alkyl, or $C_{1-4}$ hydroxyalkyl);

$R_2$, $R_3$ and $R_5$ are each independently H, halogen, $C_{1-4}$ alkyl, or $C_{6-24}$ aryl;

$R_6$ is H, OH, $C_{1-6}$ alkyl, phenyl, halogen, carboxy, carboxaldehyde, nitro, amino, $C_{1-6}$ alkoxy, dialkylaminoalkyl (in which the alkyl groups contain 1–6 carbon atoms), $C_{1-6}$ hydroxyalkyl, or $C_{1-6}$ alkenyl and m=1–4.

15. The method of claim 16 in which the composition also contains at least one coupler or developer selected from the group consisting of phenylenediamines, aminophenols, diphenols, and naphthols.

16. The method of claim 17 wherein the compound is a coupler named 1-(2-hydroxy-4-aminophenyl)pyrrole.

17. The method of claim 17 wherein the compound is a developer named 1-(2-hydroxyethylamino-5-aminophenyl)pyrrole.

* * * * *

UNITED STATES PATENT AND TRADEMARK OFFICE
CERTIFICATE OF CORRECTION

PATENT NO. : 5,019,130

DATED : May 28, 1991

INVENTOR(S) : Lawrence A. Flood

It is certified that error appears in the above-identified patent and that said Letters Patent is hereby corrected as shown below:

Column 13, claim 1, line 19, delete "precusor" and insert --precursor-- therefor.

Column 14, claim 6, line 68, in the chemical structure (V) add the substituent group "$R_3$" as shown below.

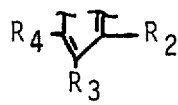

Column 15, claim 13, line 48, delete "$HC_{1-4}$" and insert --H, $C_{1-4}$-- therefor and at line 49, after "and" delete "is H or 3" and insert --H = 1-3-- therefor.

Column 15, claim 14, line 65, in the chemical structure (II) delete "$R_4$" and insert --H-- therefor and column 15, line 4, before the parenthesis ")", delete --alkyl--.

Column 18, claim 15, line 3, delete the numeral "16" and insert the numeral --14-- therefor.

Column 18, claims 16 and 17, lines 7 and 9, delete the numeral "17" and insert the numeral --14-- therefor.

Signed and Sealed this

Seventeenth Day of November, 1992

Attest:

DOUGLAS B. COMER

*Attesting Officer*     *Acting Commissioner of Patents and Trademarks*